United States Patent [19]

Mine et al.

[11] 4,209,518

[45] Jun. 24, 1980

[54] BICYCLOMYCIN AS AN ANIMAL GROWTH PROMOTANT

[75] Inventors: Kazumasa Mine, Kobe; Takeo Oshima, Habikino, both of Japan

[73] Assignee: Fujisawa Pharmaceutical Co., Ltd., Osaka, Japan

[21] Appl. No.: 942,154

[22] Filed: Sep. 14, 1978

[30] Foreign Application Priority Data

Sep. 14, 1977 [JP] Japan ............................ 52-110832

[51] Int. Cl.$^2$ ............................................ A61K 31/495
[52] U.S. Cl. .................................................. 424/250
[58] Field of Search .......................................... 424/250

[56] References Cited

PUBLICATIONS

Chemical Abstracts, vol. 78 (1973), p. 105877e.

*Primary Examiner*—V. D. Turner
*Attorney, Agent, or Firm*—Dayton R. Stemple, Jr.

[57] ABSTRACT

A new animal feed composition which comprises bicyclomycin and a new method for promoting the growth of animals, which comprises oral administration of the same to animals.

7 Claims, No Drawings

BICYCLOMYCIN AS AN ANIMAL GROWTH PROMOTANT

DESCRIPTION OF THE INVENTION

This invention relates to a new animal growth promotant. More particularly, it relates to a new animal feed composition which comprises bicyclomycin as an effective ingredient, and to methods for promoting the growth of animals and improving the rate of weight gain of animals and improving the efficiency of feed utilization by animals, which comprise the oral administration of the animal feed composition comprising bicyclomycin to animals.

Bicyclomycin to be used in this invention is a well known antibiotic having antibacterial activity against Gram-negative bacteria, having the following chemical structure [cf. The Journal of Antibiotic, 569–593, 25 (1972)].

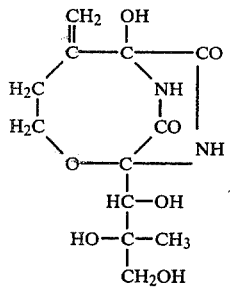

For many years, animal science industry has tried to provide an animal growth promotant, and some antibiotics have been developed and used as animal growth promotants, including, for examples, penicillins, tetracycline, bacitracin, enramycin, virginiamycin or the like. These antibiotics used as animal growth promotants up to now are characterized by their strong antimicrobial activities, especially against Gram-positive bacteria, and accordingly it has been a matter of common knowledge in the field of animal science that, when an antibiotic is used for an animal growth promotant, the antibiotic may be preferably selected from the ones which are active against Gram-positive bacteria.

However, even the animal growth promotants comprising such antibiotics can not be said to be entirely sufficient in the actual application thereof to animals due to the problems of tissue residue of the antibiotic in the animal body, which is due to its absorbability and excretion, the toxicity and so on.

Bicyclomycin to be used in this invention has a unique chemical structure, no chemical relation being noted to any groups of the known antibiotics, and is characterized by activity only against Gram-negative bacteria, it being inactive against Gram-positive bacteria. Accordingly, it has been difficult or might be impossible for a person skilled in the art to expect the effective use of the bicyclomycin for any animal growth promotant naturally from a common-sense standpoint.

In the course of pharmacological and toxicological studies of said bicyclomycin on experimental animals (e.g. rats and mice), it was found out that the bicyclomycin showed very low absorbability and extremely low toxicity when administered orally to said animals. And further, it has been observed that the successive oral administration of the bicyclomycin to said animals showed a tendency to enhance the rate of body weight gain of the treated experimental animal groups in comparison with that of the untreated control groups.

On the basis of these findings, the inventors of this invention have studied a possibility of the effective use of said bicyclomycin for animal growth promotant for economic domestic animals (e.g. chicken, pig, etc.). And, the extensive studies of the inventors have successfully resulted in providing a new animal growth promotant comprising substantially the bicyclomycin, which could be neither expected nor anticipated from a common-sense standpoint in the field of animal science as mentioned above, and the inventors have completed this invention.

Accordingly, this invention provides a new animal feed composition for promoting the growth which comprises bicyclomycin as an effective ingredient; and methods for promoting the growth of animals, improving the rate of weight gain of animals, and improving the efficiency of feed utilization by animals, which comprise the oral administration of the animal feed composition comprising bicyclomycin to animals.

Animal growth promotant of this invention which comprises essentially bicyclomycin as an effective ingredient is administered to animals in a conventional manner. Namely, the animal growth promotant of this invention is usually administered orally to animals, and the effective ingredient, bicyclomycin may be generally administered as it is or in admixture with a suitable carrier (e.g. water, kaolin, talc, calcium carbonate, lactose, etc.) or in admixture with an animal nutritious source, i.e. feed. More particularly, the effective ingredient, bicyclomycin may be administered to as a drinking water in the form of aqueous solution; or as a tablet, granule or capsule in the form of preparation which comprises bicyclomycin and the suitable non-toxic carrier as exemplified above; or as a ration in the form of the composition which comprises bicyclomycin and animal feed and sometimes the other feed additive. In the administration methods of the effective ingredient as mentioned above, it is to be understood that bicyclomycin can be used not only in its purified form but also in partially purified form.

In connection of the form of administering the animal feed composition of this invention as mentioned above, the ration comprising bicyclomycin can be prepared in a conventional manner, namely by admixing bicyclomycin with basal ration. And, as the basal ration, natural feed and assorted feed can be used, including dry feeds, liquid feed, pelleted feed and the like. As preferred basal ration, there is preferably used the assorted feed which comprises one or more conventional feeds such as corn, rice, wheat, milo, soybean meal, cottonseed meal, wheat bran, defatted rice bran, fish meal, skim milk, dried whey, oils, fats, alfalfa meal or the like and one or more of the conventional feed additives such as tricalcium carbonate, sodium chloride, choline chloride, vitamin (e.g. vitamin A, vitamin D, vitamin E, vitamin $B_1$, vitamin $B_2$, vitamin $B_6$, vitamin $B_{12}$, calcium pantothenate, nicotinamide, folic acid, etc.), amino acid (e.g. lysine, methionine, etc.), mineral source (e.g. magnesium sulfate, ferrous sulfate, copper sulfate, zinc sulfate, potassium iodide, cobalt sulfate, etc.) or the like. The amounts of the bicyclomycin in the basal rations which are fed to the animals may be varied over a very wide range depending upon the kind, nature, growth period, etc. of the animals, and the breeding method, breeding circumstance, breeding seasons of the animals and the like. Levels which are construed as preferably and anticipated to yield the preferred growth are in an amount between about 0.5 p.p.m. and about 500 p.p.m., more preferably between about 1 p.p.m. and about 200 p.p.m.

As to the other form of administration, the capsules can be prepared by filling the bicyclomycin with any desired form of it. If desired, the bicyclomycin is diluted with an inert powdered diluent (e.g. sugar, starch, cellulose, etc.) in a conventional manner in order to increase its volume for convenience in filling capsules. The tablet can be prepared in a conventional manner, for example, by admixing the bicyclomycin with a base (e.g. lactose, sugar, mannitol, starch, sodium chloride, etc.), a disintegrator (e.g. starch, alginic acid, sodium lauryl sulfate, etc.), a binder (e.g. gelatin, gums, starch, dextrin, etc.), a lubricant (magnesium stearate, talc, paraffin wax, polyethylene glycol, etc.). The granules also can be prepared in a conventional manner. The drinking water comprising bicyclomycin can be prepared by simply dissolving the bicyclomycin to the water in the proper amount.

Dosage of the animal feed composition as mentioned above to animals is varied depending upon the kind, nature, growth period, etc. of the animals, and its preferred dosage may usually be selected from the range of about 0.1–40 mg/kg/day as the amount of bicyclomicin.

Further, it is to be noted that the animal feed composition as prepared above can also include, as the other feed additives than those as mentioned above, for examples, the other antibiotics, pesticide, fungicide, coccidiostat, antioxidant, natural pigment and the like. As preferred antibiotic to be added, there are exemplified by thiopeptin, enramycin, bacitracin, mikamycin, fradiomycin, flavomycin, virginiamycin, kitasamycin, tylosin, quebemycin and the like, which are useful as animal growth promotants and/or veterinary drugs. Furthermore, it is usual to treat animals with a variety of growth promotants, disease-preventives and disease treatments throughout their lives, and such drugs are often used in combination. Accordingly, the new methods of this invention may be practiced in combination with the other treatments.

The animal growth promotant of this invention can be administered effectively to animals such as poultry (e.g. chicken, turkey, duck, quail, etc.), cattle pig, sheep, goat, rabbit, mink, and the like. The breeding of animals using the animal feed composition of this invention can be conducted in a conventional manner. In the course of breeding of animals, it is to be understood that, when the animals suffer from infectious diseases (e.g. diarrhea) caused by pathogenic Gram-negative bacteria (e.g Salmonella) or have the risk of suffering from such diseases especially in bad breeding surroundings, said diseases of animals also can be effectively treated or prevented with the animal growth promotant of this invention.

The animal growth promotant of this invention promotes the growth of animals so that the rate of weight gain of animal can be improved, and also improves the efficiency of feed utilization by animals. In addition to this, the animal growth promotant of this invention is more improved in the point of the tissue residue of the antibiotic in the animal body, especially in egg and flesh. Namely, the effective ingredient, bicyclomycin, when the animal feed composition is fed to animals at such levels as stated hereinabove, is difficult to be absorbed into the interior of the body from the digestive organs (e.g. the intestines), and are almost undetectable in the serum and the tissues of the internal organs of the animals. Moreover, said bicyclomycin per se is much lower in its toxicity. Accordingly the effective ingredient, bicyclomycin, when fed in admixture with the basal rations at appropriate level, has neither unfavorable nor undesirable influences upon animals and does not remain in the tissue of animals such as flesh. From the usefulness and advantage as stated above, the animal growth promotant of this invention can be said to be a more improved animal promotant as compared with the known ones and therefore can be used with safety for promoting the growth of animals.

The following Examples are given to illustrate this invention, but it should be understood that they are not intended to limit this invention.

EXAMPLE 1

Day-old male broiler chicks (White Rock×White Cornish cross breed) were divided into two groups, i.e. treatment group and control group, each of which consisted of fifty chicks. The control group was fed for initial 5 weeks with Feed Composition I and for further 3 weeks with Feed Composition II, both of which contain the given amount of bicyclomycin as listed in the Table 1-(b). The control group was fed in the same manner as the treatment group with Feed Compositions I and then II, both of which do not contain bicyclomycin as noted in the Table 1-(b). The said Feed Compositions were continuously fed to the chickens, and their growth and the efficiency of feed utilization by the chickens were observed for 8 weeks.

The results are shown in the following table.

Table 1-(a):

| | Experimental Result | |
|---|---|---|
| | Treatment Group | Control Group |
| Average initial body weight (g) | 44 | 44 |
| Average final body weight (g) at 8 weeks of age | 1,886 | 1,751 |
| Average body weight gain (g) at 8 weeks of age | 1,842 | 1,707 |
| Efficiency of feed utilization* | 2.34 | 2.35 |

*Note:

$$\text{Efficiency of feed utilization} = \frac{\text{Feed Compositions (g) utilized for 8 weeks duration.}}{\text{Average body weight gain (g)}}$$

Table 1-(b):

| | Feed Composition | |
|---|---|---|
| Composition Ingredient (%) | Feed Composition I to bo fed to chickens of 0 to 4 weeks of age | Feed Composition II to be fed to chickens of 5 to weeks of age |
| Corn | 45 | 40 |
| Milo | 20 | 20 |
| Soybean meal | 23 | 20 |
| Fish meal | 7 | 5 |
| Defatted rice bran | 0 | 6 |
| Plant oil | 0 | 4 |
| Alfalfa meal | 2.4 | 2.4 |
| Calcium carbonate | 1.3 | 1.2 |
| Tricalcium phosphate | 0.7 | 0.8 |
| Sodium chloride | 0.25 | 0.25 |
| Vitamiin A D$_3$ premix | 0.05 | 0.05 |
| Vitamin B premix*[1] | 0.09 | 0.09 |
| Trace mineral premix*[2] | 0.03 | 0.03 |
| Amprol Plus (coccidiostat, trade | 0.13 | 0.08 |

Table 1-(b):-continued

| Composition Ingredient (%) | Feed Composition I to bo fed to chickens of 0 to 4 weeks of age | Feed Composition II to be fed to chickens of 5 to weeks of age |
|---|---|---|
| mark made by Merck & Co.) | | |
| DL-Methionine | 0.05 | 0.05 |
| Ethoxyquin (50% preparation) | 0 | 0.05 |
| Bicyclomycin[3] | 1 ppm | 1 ppm |

Note:
[1] Vitamin B premix is composed of vitamin $B_1$, vitamin $B_2$, vitamin $B_6$, vitamin $B_{12}$, biotin, folic acid and calcium pantothenate.
[2] Trace mineral premix is composed of ferrous sulfate, manganese sulfate, zinc sulfate, copper sulfate, cobalt sulfate and potassium iodide.

EXAMPLE 2

Day-old broiler chicks (White Rock × White Cornish cross breed) were divided into two groups, i.e., treatment group and control group, each of which consisted of 75 male and 75 female chicks. The control group and the treatment group were continuously fed for the initial 5 weeks with Feed Composition I and for further 1 week with Feed Composition II, respectively, both of which are listed below, and their growth and the efficiency of feed utilization were observed for 6 weeks.

The results are shown in the following table.

Table 2-(a):

| Experimental Result | Treatment Group | Control Group |
|---|---|---|
| Average initial body weight (g) | 41 | 41 |
| Average final body weight (g) at 6 weeks of age | 1,121 | 1,054 |
| Average body weight gain (g) at 6 weeks of age | 1,080 | 1,013 |
| Efficiency of feed utilization* | 2.11 | 2.22 |

*Note:
$$\text{Efficiency of feed utilization} = \frac{\text{Feed Compositions (g) utilized for 6 weeks duration}}{\text{Average body weight gain (g)}}$$

Table 2-(b):

| Ingredient (%) | Feed Composition I to be fed to chickens of 0 to 4 weeks of age | Feed Composition II to be fed to chickens of 5 to 6 weeks of age |
|---|---|---|
| Corn | 55.6 | 56.25 |
| Soybean meal | 30.0 | 23.0 |
| Defatted rice bran | 0 | 8.0 |
| Alfalfa meal | 1.5 | 2.3 |
| Fish meal | 8.0 | 5.0 |
| Fats and oils | 2.5 | 3.0 |
| Calcium carbonate | 1.0 | 1.0 |
| Tricalcium phosphate | 0.5 | 0.3 |
| Sodium chloride | 0.25 | 0.25 |
| Vitamin $AD_3E$ premix | 0.1 | 0.1 |
| Vitamin B premix [1] | 0.3 | 0.3 |
| Trace mineral premix [2] | 0.1 | 0.1 |
| DL-Methionine | 0.1 | 0.1 |
| Lysine | 0 | 0.05 |
| Bicyclomycin | 20 ppm | 20 ppm |

Note:
[1] This vitamin B premix is the same as that of Example 1.
[2] This trace mineral premix is the same as that of Example 1.
[3] Composition I and II fed to the control group does not comprise bicyclomycin.

EXAMPLE 3

Day-old broiler chicks (White Rock × White Cornish cross breed) were divided into two groups, i.e., control group and treatment group, each of which consisted of 40 male and 40 female chicks. The control group and the treatment group were continuously fed for the 5 weeks with Feed Composition I, which is the same as that of Example 2, excepting the concentration of bicyclomycin is 160 ppm (Note: Feed Composition used for the control group does not contain bicyclomycin), and their growth and the efficiency of feed utilization were observed for 5 weeks.

The results are shown in the following table.

Table 3

| | Treatment Group | Control Group |
|---|---|---|
| Average initial body weight (g) | 37 | 37 |
| Average final body weight (g) at 5 weeks of age | 1,039 | 991 |
| Average body weight gain (g) at 5 weeks of age | 1,002 | 954 |
| Efficiency of feed utilization* | 1.78 | 1.79 |

*Note:
$$\text{Efficiency of feed utilization} = \frac{\text{Feed Composition (g) utilized for 5 weeks duration}}{\text{Average body weight gain (g)}}$$

EXAMPLE 4

40 Day-old Landrace pigs were divided into four groups, i.e., three of treatment groups (i.e. Treatment Groups I, II and III) and control group, each of which consisted of five barrows and four female pigs. These pigs were continuously fed with Feed Composition (milk replacer) described in Table 4-(b) and their growth and efficiency of feed utilization were observed for 4 weeks. The results are shown in the following table.

Table 4-(a):

| Experimental Result | Treatment Group | | | Control Group |
|---|---|---|---|---|
| | I | II | III | |
| Average initial body weight (kg) | 9.97 | 9.96 | 9.97 | 9.96 |
| Average final body weight (kg) at the 4th week after the starting of the feeding | 26.82 | 27.02 | 27.96 | 24.33 |
| Average body weight gain (kg) at the 4th week after the starting of the feeding | 16.85 | 17.06 | 17.99 | 14.37 |
| Efficiency of feed | 1.802 | 1.861 | 1.775 | 1.943 |

Table 4-(a):-continued

| | Experimental Result | | | |
|---|---|---|---|---|
| | Treatment Group | | | Control Group |
| | I | II | III | |
| utilization* | | | | |

*Note:

$$\text{Efficiency of feed utilization} = \frac{\text{Feed Compositions (kg) utilized for 4 weeks duration}}{\text{Average body weight gain (kg)}}$$

Table 4-(b):

| Feed Composition Basal feed composition | |
|---|---|
| Ingredient | % |
| Corr | 50 |
| Milo | 5 |
| Wheat flour | 5 |
| Soybean oil cake | 19 |
| Dried Whey | 6 |
| Skim milk | 4 |
| Fish meal | 3 |
| Glucose | 2 |
| Beef tallow | 1 |
| Defatted rice bran | 2 |
| Tricalcium phosphate | 0.9 |
| Calcium carbonate | 1.2 |
| Sodium chloride | 0.4 |
| DL-Methionine | 0.05 |
| Lysine hydrochloride | 0.1 |
| Vitamin A D$_3$ E premix | 0.05 |
| Vitamin B premix*[1] | 0.2 |
| Trace mineral premix*[2] | 0.1 |

Note:
*[1], *[2]: see Example 1

| Feed Composition fed to animals | |
|---|---|
| Feed Composition fed to Treatment Group I | The above basal feed + bicyclomycin 20 ppm |
| Feed Composition fed to Treatment Group II | The above basal feed + bicyclomycin 40 ppm |
| Feed Composition fed to Treatment Group III | The above basal feed + bicyclomycin 80 ppm |
| Feed Composition fed to Control Group | The above basal feed |

EXAMPLE 5

50–60 Day-old Landrace pigs were divided into four groups, i.e., three of treatment groups (Treatment Groups I, II and III) and Control group, each of which consisted of five barrows and five female pigs. These pigs were continuously fed with Feed Composition described in Table 5-(b), and their growth and efficiency of feed utilization were observed for 10 weeks. The results are shown in the following table.

Table 5-(a):

| | Experimental Result | | | |
|---|---|---|---|---|
| | Treatment Group | | | Control Group |
| | I | II | III | |
| Average initial body weight (kg) | 13.6 | 13.6 | 13.6 | 13.6 |
| Average final body weight (kg) at the 10th week after the starting of the feeding | 60.3 | 62.9 | 64.6 | 57.9 |
| Average weight gain (kg) at the 10th week after the starting of the feeding | 46.7 | 49.3 | 51.0 | 44.3 |
| Efficiency of feed utilization* | 2.86 | 2.86 | 2.82 | 3.03 |

*Note:

$$\text{Efficiency of feed utilization} = \frac{\text{Feed Compositions (kg) utilized for 10 weeks duration}}{\text{Average body weight gain (kg)}}$$

Table 5-(b):

| Feed Composition Basal feed composition | |
|---|---|
| Ingredient | % |
| Corr | 55 |
| Milo | 15 |
| Wheat flour | 7 |
| Soybean oil cake | 12 |
| Peanut meal | 2 |
| Fish meal | 4 |
| Defatted rice bran | 2.25 |
| Tricalcium phosphate | 0.8 |
| Calcium carbonate | 1.2 |
| Sodium chloride | 0.4 |
| DL-Methionine | 0.05 |
| Lysine hydrochloride | 0.05 |
| Vitamin A D$_3$E premix | 0.05 |
| Vitamin B premix*[1] | 0.1 |
| Trace mineral premix*[2] | 0.1 |

Note:
*[1], *[2]: see Example 1

| Feed Composition fed to animals | |
|---|---|
| Feed Composition fed to Treatment Group I | The above basal feed + bicyclomycin 10 ppm |
| Feed Composition fed to Treatment Group II | The above basal feed + bicyclomycin 20 ppm |
| Feed Composition fed to Treatment Group III | The above basal feed + bicyclomycin 40 ppm |
| Feed Composition fed to Control Group | The above basal feed |

EXAMPLE 6

30 Days-old pigs [LW·H, i.e. (Landrace ♀ × Large Yorkshire ♂) ♀ × Hampshire ♂ cross breed] were divided into four groups, i.e., three of treatment groups (Treatment Groups I, II and III) and Control group, each of which consisted of five barrows and five female pigs. These pigs were continuously fed with Feed Composition described in Table 6-(b), and their growth and efficiency of feed utilization were observed for 6 weeks. The results are shown in the following table.

Table 6-(a):

| | Experimental Result | | | |
|---|---|---|---|---|
| | Treatment Group | | | Control Group |
| | I | II | III | |
| Average initial weight (kg) | 5.99 | 5.84 | 5.96 | 5.96 |
| Average weight (kg) at the 6th week after the starting of the feeding | 21.43 | 21.37 | 23.15 | 20.70 |
| Average weight gain (kg) at the 6th week after the starting of the feeding | 15.44 | 15.53 | 17.19 | 14.74 |
| Efficiency of feed | 2.02 | 2.10 | 1.59 | 1.96 |

Table 6-(a):-continued

| | Experimental Result | | | |
|---|---|---|---|---|
| | Treatment Group | | | |
| | I | II | III | Control Group |
| utilization* | | | | |

*Note:

$$\text{Efficiency of feed utilization} = \frac{\text{Feed Compositions utilized for 6 weeks duration (kg)}}{\text{Average body weight gain (kg)}}$$

Table 6-(b):

| Feed Composition | |
|---|---|
| Basal feed composition | |
| The basal feed composition is the same as that of Example 4. | |
| Feed Composition | |
| Feed Composition fed to Treatment Group I | The above basal feed + bicyclomycin 5 ppm + thiopeptin* 20 ppm |
| Feed Composition fed to Treatment Group II | The above basal feed + bicyclomycin 10 ppm + thiopeptin 20 ppm |
| Feed Composition fed to Treatment Group III | The above basal feed + bicyclomycin 20 ppm + thiopeptin 20 ppm |
| Feed Composition fed to Control Group | The above basal feed + thiopeptin 20 ppm |

*Note:
Thiopeptin is a known antibiotic active against Gram-positive bacteria [cf. Antimicrobial Agents and Chemotherapy, Pages 496-503, Vol. 1, No. 6 (1972)]

The following examples of the feed compositions are given for the purpose of illustrating this invention.

| Feed composition 1 | |
|---|---|
| Ingredient | |
| Corn | 601 kg |
| Defatted soybean | 250 kg |
| Alfalfa meal | 20 kg |
| Fish meal | 80 kg |
| Plant oil | 25 kg |
| Calcium carbonate | 10 kg |
| Tricalcium phosphate | 5 kg |
| Sodium chloride | 3 kg |
| Vitamin A D$_3$ E premix | 1 kg |
| Vitamin B premix*[1] | 3 kg |
| DL-Methionine | 1 kg |
| Trace mineral premix*[2] | 1 kg |
| Zoalene 10% preparation (coccidiostat, trade name, made by Tanabe Seiyaku Co., Ltd.) | 1.25 kg |

| Feed composition 1 | |
|---|---|
| Ingredient | |
| Bicyclomycin | 10 g |

Note:
*[1], *[2]: see Example 1

The above ingredients were equally mixed to give a animal feed composition.

| Feed composition 2 | |
|---|---|
| Ingredient | |
| Skim milk | 270 kg |
| Dried whey | 100 kg |
| Fish meal | 50 kg |
| Wheat flour | 350 kg |
| Glucose | 50 kg |
| Tallow | 30 kg |
| Dried yeast | 100 kg |
| Starch | 21 kg |
| Casein sodium | 10 kg |
| Tricalcium phosphate | 10 kg |
| Sodium chloride | 4 kg |
| DL-Methionine | 500 g |
| Lysine hydrochloride | 1 kg |
| Vitamin A D$_3$ E premix | 2 kg |
| Vitamin B premix*[1] | 2 kg |
| Trace mineral premix*[2] | 1 kg |
| Bicyclomycin | 50 g |

Note:
*[1], *[2]: see Example 1

The above ingredients were equally mixed to give a animal feed composition (milk replacer).

What we claim is:

1. A method for promoting the growth of growing animals, which comprises orally administering a feed composition to said animals comprising a sufficient amount of bicyclomycin to promote growth and a compatible animal nutrition source.

2. A method for improving the rate of weight gain of growing animals, which comprises orally administering to said animals a feed composition comprising a sufficient amount of bicyclomycin to increase said rate of weight gain and a compatible animal nutrition source.

3. A method for improving the efficiency of feed utilization by growing animals, which comprises orally administering to said animals a feed composition comprising a sufficient amount of bicyclomycin to improve said efficiency and a compatible animal nutrition source.

4. The method of claim 1, 2 or 3 wherein the amount of bicyclomycin is 0.5 to 500 p.p.m. of said composition.

5. The method of claim 1, 2 or 3 wherein the amount of bicyclomycin is 1.0 to 200 p.p.m. of said composition.

6. The method of claim 1, 2 or 3 wherein said animals are poultry or cattle.

7. The method according to claims 1, 2 or 3 wherein said animals are chickens or pigs.

* * * * *

UNITED STATES PATENT AND TRADEMARK OFFICE
CERTIFICATE OF CORRECTION

PATENT NO. : 4,209,518
DATED : June 24, 1980
INVENTOR(S) : Kazumasa Mine and Takeo Oshima It is certified that error appears in the above–identified patent and that said Letters Patent are hereby corrected as shown below:

Col. 4, line 53, "bo" should read -- be --.
Col. 4, line 54, after "5 to", insert -- 8 --.
Col. 5, line 17, insert -- *3) Compositions I and II fed to the control group does not comprise bicyclomycin. --.
Col. 5, line 53, above "ingredient", insert -- composition --.
Col. 7, line 16, "Corr" should read -- Corn --.
Col. 8, line 16, "Corr" should read -- Corn --.

Signed and Sealed this

Seventh Day of October 1980

[SEAL]

Attest:

SIDNEY A. DIAMOND

Attesting Officer

Commissioner of Patents and Trademarks